United States Patent [19]

Brazeau et al.

[11] Patent Number: 6,020,311
[45] Date of Patent: *Feb. 1, 2000

[54] GRF ANALOGS WITH INCREASED BIOLOGICAL POTENCY

[75] Inventors: Paul Brazeau, Montréal; Denis Gravel, St-Lambert, both of Canada

[73] Assignee: Theratechnologies, Inc., Montreal, Canada

[ * ] Notice: This patent is subject to a terminal disclaimer.

[21] Appl. No.: 09/148,982

[22] Filed: Sep. 8, 1998

Related U.S. Application Data

[63] Continuation-in-part of application No. 08/702,113, Aug. 23, 1996, Pat. No. 5,939,386, and application No. 08/702,114, Aug. 23, 1996, Pat. No. 5,861,379, which is a continuation-in-part of application No. 08/651,645, May 22, 1996, abandoned, and application No. 08/453,067, May 26, 1995, abandoned.

[51] Int. Cl.[7] .............................. A61K 38/25; C07K 14/60
[52] U.S. Cl. .............................. 514/12; 530/324; 530/399
[58] Field of Search ................... 514/12; 530/324, 530/399; 930/120

[56] References Cited

U.S. PATENT DOCUMENTS 5,861,379  1/1999  Ibea et al. ................................. 514/12

*Primary Examiner*—Michael P. Woodward
*Assistant Examiner*—Anish Gupta
*Attorney, Agent, or Firm*—Evenson, McKeown, Edwards & Lenahan, P.L.L.C.

[57] ABSTRACT

The present invention relates to chimeric fatty body-GRF analogs with increased biological potency, their application as anabolic agents and in the diagnosis and treatment of growth hormone deficiencies. The chimeric fatty body-GRF analogs include an hydrophobic moiety (tail), and can be prepared, either by anchoring at least one hydrophobic tail to the GRF, in the chemical synthesis of GRF. The GRF analogs of the present invention are biodegradable, non-immunogenic and exhibit an improved anabolic potency with a reduced dosage and prolonged activity.

10 Claims, 8 Drawing Sheets

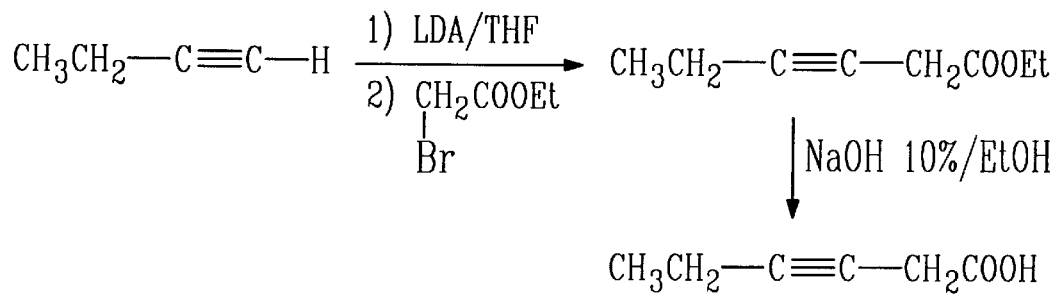
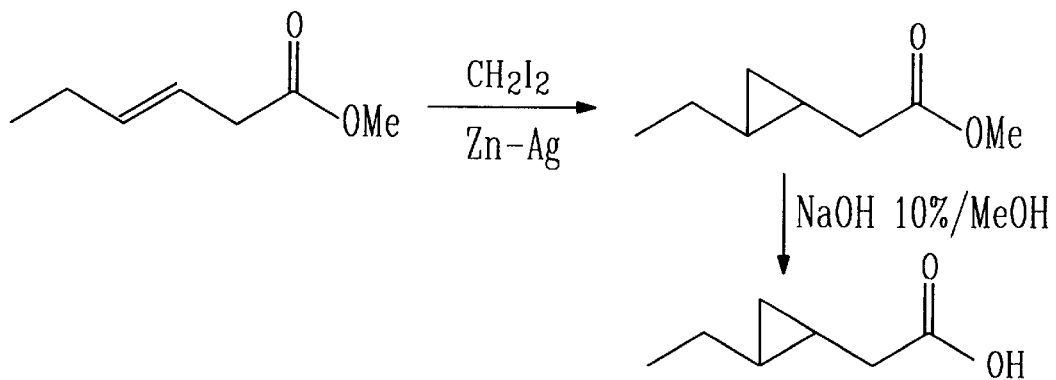
FIG. 6A

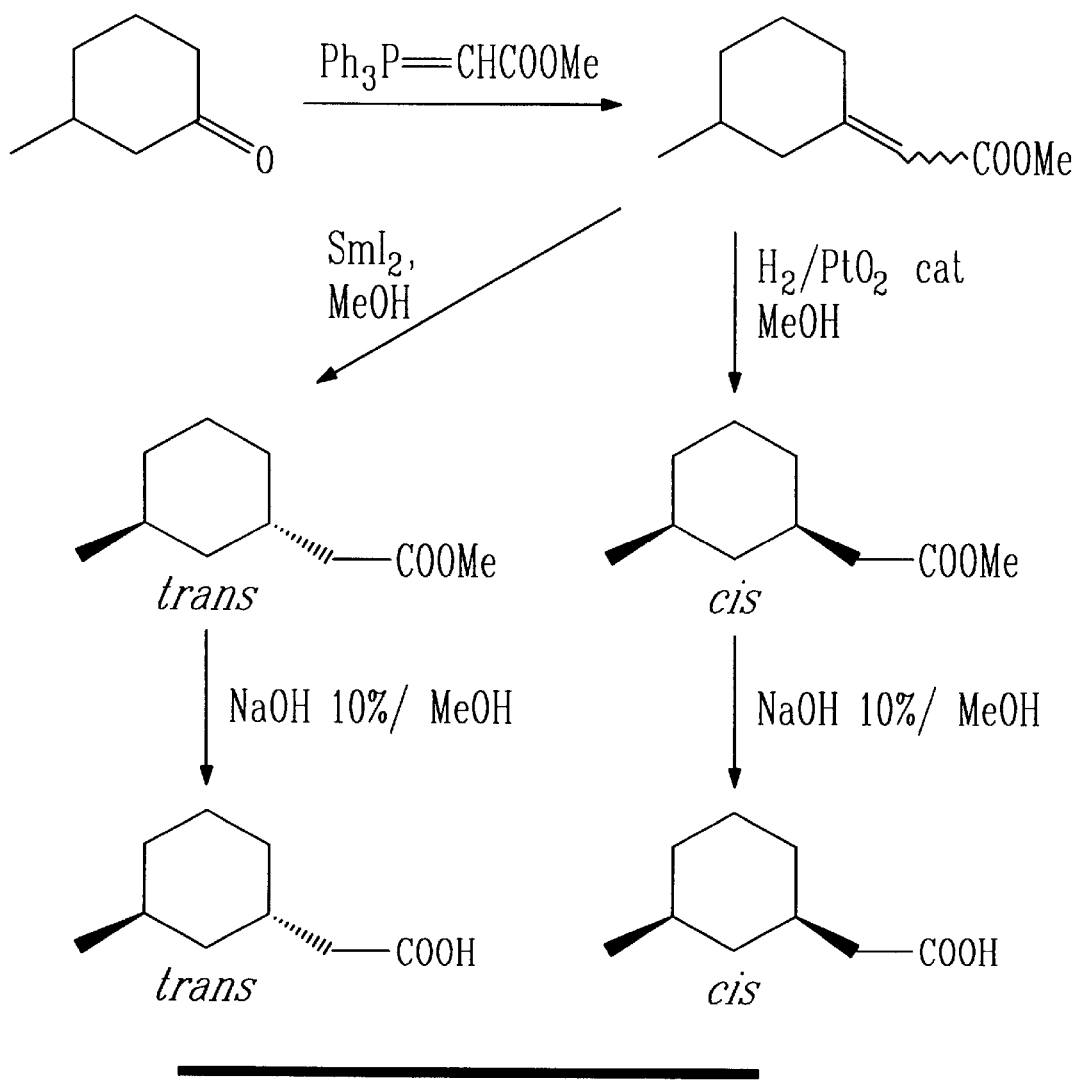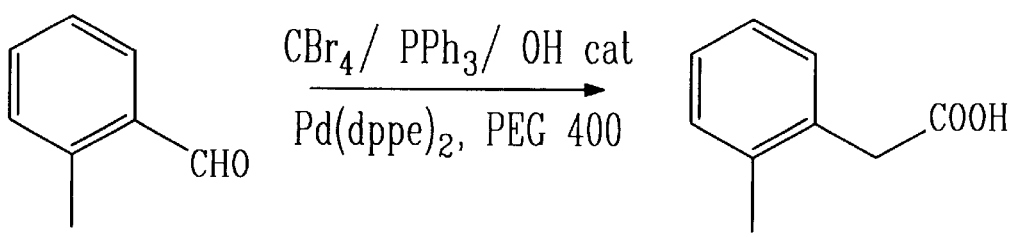
FIG. 6C

GRF ANALOGS WITH INCREASED BIOLOGICAL POTENCY

RELATED APPLICATIONS

This application is a continuation-in-part of application Ser. Nos. 08/702,113 filed Aug. 23, 1996 and now U.S. Pat. Nos. 5,939,386 and 08/702,114 filed on Aug. 23, 1996 and now U.S. Pat. No. 5,861,379 and which are continuations in part of application Ser. No. 08/651,645 filed on May 22, 1996, which is abandoned and is a continuation-in-part of application Ser. No. 08/453,067 filed on May 26, 1995 and which is abandoned and all above applications are all incorporated by reference.

BACKGROUND OF THE INVENTION (a) Field of the Invention

The invention relates to hydrophobic GRF analogs with increased biological potency and prolonged activity, their application as anabolic agents and treatment of growth hormone deficiencies.

(b) Description of Prior Art

Growth hormone (GH) or somatotropin, secreted by the pituitary gland constitute a family of hormones which biological activity is fundamental for the linear growth of a young organism but also for the maintenance of the integrity at its adult state. GH acts directly or indirectly on the peripheral organs by stimulating the synthesis of growth factors (insulin-like growth factor-I or IGF-I) or of their receptors (epidermal growth factor or EGF). The direct action of GH is of the type referred to as anti-insulinic, which favors the lipolysis at the level of adipose tissues. Through its action on IGF-I (somatomedin C) synthesis and secretion, GH stimulate the growth of the cartilage and the bones (structural growth), the protein synthesis and the cellular proliferation in multiple peripheral organs, including muscles and the skin. Through its biological activity, GH participates within adults in the maintenance of a protein anabolism state, and plays a primary role in the tissue regeneration phenomenon after a trauma.

The decrease of GH secretion with age, demonstrated in humans and animals, favors a metabolic shift towards catabolism which initiates or participates in the aging of an organism. The loss in muscle mass, the accumulation of adipose tissue, the bone demineralization, the loss of tissue regeneration capacity after an injury, which are observed in elderly, correlate with the decrease in the secretion of GH.

GH is thus a physiological anabolic agent absolutely necessary for the linear growth of children and which controls the protein metabolism in adults.

The secretion of GH by the pituitary gland is principally controlled by two hypothalamic peptides, somatostatin and growth hormone-releasing factor (GRF). Somatostatin inhibits its secretion, whereas GRF stimulates it.

The human GH has been produced by genetic engineering for about ten years. Until recently most of the uses of GH were concerned with growth delay in children and now the uses of GH in adults are being studied. The pharmacological uses of GH and GRF may be classified in the following three major categories.

Children Growth

Treatments with recombinant human growth hormone have been shown to stimulate growth in children with pituitary dwarfism, renal insufficiencies, Turner's syndrome and short stature. Recombinant human GH is presently commercialized as an "orphan drug" in Europe and in the United States for children's growth retardation caused by a GH deficiency and for children's renal insufficiencies. The other uses are under clinical trial investigation.

Long Term Treatment for Adults and Elderly Patients

A decrease in GH secretion causes changes in body composition during aging. Preliminary studies of one-year treatment with recombinant human GH reported an increase in the muscle mass and in the thickness of skin, a decrease in fat mass with a slight increase in bone density in a population of aged patients. With respect to osteoporosis, recent studies suggest that recombinant human GH does not increase bone mineralization but it is suggested that it may prevent bone demineralization in post-menopausal women. Further studies are currently underway to demonstrate this theory.

Short Term Treatment in Adults and Elderly Patients

In preclinical and clinical studies, growth hormone has been shown to stimulate protein anabolism in wound and bone healing in cases of burn, AIDS and cancer.

GH and GRF are also intended for veterinary pharmacological uses. Both GH and GRF stimulate growth in pigs during its fattening period by favoring the deposition of muscle tissue instead of adipose tissue and increase milk production in cows, and this without any undesired side effects which would endanger the health of the animals, and without any residue in the meat or milk being produced. The bovine somatotropin (BST) is presently commercialized in the United States.

Most of the clinical studies undertaken were conducted with recombinant GH. GRF is considered as a second generation product destined to replace, in the near future, the use of GH in most instances. Accordingly, the use of GRF presents a number of advantages over the use of GH per se.

Physiological Advantages

Growth hormone (GH) is secreted by the pituitary gland in a pulse fashion. Since this rhythm of secretion is crucial for an optimal biological activity, the administration of GH to correspond to its natural mode of secretion is difficult to achieve. When GRF is administered in a continuous fashion as a slow releasing preparation or as an infusion, it increases GH secretion while respecting its pulsatility.

The recombinant GH which is presently commercialized is the 22 kDa form whereas GRF induces the synthesis and secretion from the pituitary gland of all the chemical isomers of GH which participate in a wider range of biological activities.

A treatment with GH results in a decreased capacity of the pituitary gland to secrete endogenous growth hormone, and the GH response to GRF is diminished after such a treatment. On the contrary, a treatment with GRF does not present this disadvantage, its trophic action on the pituitary gland increases this gland's secreting capacity in normal animals and in patients with somatotroph insufficiency.

Economical Advantages

The production of GH by genetic engineering is very expensive for clinical use. In particular, there are risks of contamination of these commercial preparation with material from the bacterial strain used. These bacterial contaminants may be pyrogens or may result in immunogenic reactions in patients. The purification of the recombinant product is carried out by following a plurality of successive chromatography steps. The drastic purity criteria imposed by regulatory agencies necessitate multiple quality control steps.

On the other hand, the synthesis of GRF is of chemical nature. The synthesis is carried out in a solid phase and its purification is done in a single step using high performance liquid chromatography (HPLC). Also the quantity of GRF to be administered is much less than the quantity of GH for the same biological result.

Even with all these advantages, GRF is still not commercialized as a therapeutic agent to date, mainly because of its instability. The human GRF is a peptide of 44 amino acids of the following sequence:

```
Tyr Ala Asp Ala Ile Phe Thr Asn Ser Tyr Arg Lys Val Leu Gly Gln   (SEQ ID NO:1)
1            5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu-NH2.
            35                  40
```

The minimum active core is hGRF (1–29)NH$_2$

```
Tyr Ala Asp Ala Ile Phe Thr Asn Ser Tyr Arg Lys Val Leu Gly Gln(SEQ ID NO:2)
1            5                   10                  15

Leu Ser Ala Arg Lys Leu Leu Gln Asp Ile Met Ser Arg.
            20                  25
```

As for many peptides, hGRF (1–29)NH$_2$ is rapidly degraded in a serum medium and its metabolites have no residual biological activity. It has been well established that the action of enzymes, namely that of dipeptidylaminopeptidase type IV, in a blood medium results in the hydrolysis of the peptide bond Ala$^2$-Asp$^3$ of GRF. This hydrolysis results in a multitude of negative consequences which were the subject of many studies reported in the literature. Essentially, this hydrolysis leads to the formation of truncated peptides of specific activity reduced to less than 1/1000 of the biological activity.

Clinical studies with children and adults have confirmed that natural hGRF (1–44)NH$_2$ or the active fragment hGRF (1–29)NH$_2$ are not potent enough to produce equal effects corresponding to those of recombinant GH.

It is well known that the anchoring of hydrophobic groups, such as —NEt$_2$ at the C-terminal of a peptidic sequence can result in a significantly increased specific activity. In terms of hydrophobicity, these results are contradicted by a fair number recent works such as those of Muranichi (S. Muranichi et al., 1991, *Pharm. Res.*, 8:649–652) which stress the inefficacy of the lauroyl group as a hydrophobic group at the N-terminal to create small peptide analogs having the desired biological activity. Hence, the contradictory investigations of the prior art failed to address the issue of finding a more potent GRF analog using hydrophobic residues.

Gaudreau et al. (P. Gaudreau et al., 1992, *J. Med. Chem.*, 35(10),:1864–1869) describe the affinity of acetyl-, 6-aminohexanoyl-, and 8-aminooctanoyl-GRF(1–29)NH$_2$ with the rat pituitary receptor. In this report, none of the fatty acid-GRF compounds tested exhibited a higher affinity than hGRF(1–29)NH$_2$ itself, and the authors concluded that " . . . modifications to increase the hydrophobic character at the N-terminus of hGRF(1–29)NH$_2$ do not constitute a suitable approach to increase receptor affinity.".

Coy et al. (D. H. Cow et al., 1987, *J. Med. Chem.*, 30:219–222) describe an acetyl-GRF peptide with an increased biological activity on a rat model, more particularly on a rat anesthetized with sodium pentobarbital. The in vitro GH response by cultured rat pituitary cells was also analyzed. However, these authors did not synthesize and test fatty acid-GRF analogs with a carbon chain longer than two (2) carbon atoms (acetyl group) added at the N-terminus region of the GRF and acetyl cannot be considered a hydrophobic group.

Up to now, most of the GRF analogs described (including those of Gaudreau et al. and those of Coy et al.) have been tested in rat models, either in vitro or in vivo. Since human and rat GRF(1–29)NH$_2$ are markedly different, the structure-activity relationships of GRF are different in both species. Therefore, it is not possible to extrapolate results obtained in rats to humans.

Accordingly, it is necessary to design GRF analogs with improved anabolic potency and having a prolonged activity. This increased potency could result from a resistance to serum degradation and/or from hyperagonistic properties.

It would be highly desirable to be provided with GRF analogs with increased anabolic potency.

SUMMARY OF THE INVENTION

One aim of the present invention is to provide new biodegradable GRF analogs with improved biological potency and prolonged activity.

Another aim of the present invention is to provide GRF analogs with increased anabolic potency and prolonged activity, i.e. capable to substantially elevate insulin-like growth factor I (IGF-I) levels when chronically administered in humans and animals.

Another aim of the present invention is to provide a means to render any GRF analog more biologically potent and with a prolonged activity.

Another aim of the present invention is to provide a method of producing active GRF analogs with improved anabolic potency and prolonged activity.

The present invention relates to the preparation of hydrophobic GRF analogs. These chimeric analogs include an hydrophobic moiety (tail), and can be prepared, either by anchoring one or several hydrophobic tails to the GRF, or by substituting one or several amino-acids by a pseudomicellar residue in the chemical synthesis of GRF. The GRF analogs in accordance with the present invention are characterized in that:

a) These analogs possess an enhanced biological activity; specifically, they are able to markedly increase GH and IGF-I blood levels when administered in an animal model closely related to human. This characteristic is particularly advantageous in that it results in a reduced dosage of an hyperactive compound being administered to the patient, thus improving treatment efficacy and reducing treatment costs.

b) Both natural amino acid and hydrophobic substances, such as fatty acids, are used for the chemical synthesis of the GRF analogs.

c) They present a high biological activity at infinitely small dosages.

d) They remain active for a prolonged period of time, with a high biological activity.

The use of fatty bodies in accordance with the present invention results in GRF analogs which overcome all the drawbacks of the prior art. The GRF analogs of the present invention exhibit an improved anabolic potency with a reduced dosage and have a prolonged activity. Furthermore, the present invention deals with GRF and any of its analogs, truncated or substituted.

In accordance with the present invention there is provided a hydrophobic GRF analog of formula A:

X—GRF-peptide    (A)

wherein;

the GRF peptide is a peptide of formula B

A1–A2-Asp-Ala-Ile-Phe-Thr-A8-Ser-Tyr-Arg-Lys-A13-Leu-A15-Gln-Leu-A18-Ala-Arg-Lys-Leu-Leu-A24–A25-Ile-A27–A28-Arg-A30-$R_0$    (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;
A30 is a bond or any amino acid sequence of 1 up to 15 residues;
$R_0$ is $NH_2$ or $NH-(CH_2)n\text{-}CONH_2$, with n=1 to 12 and;
X is hydrophobic tail anchored via an amide bond and said hydrophobic tail defining a backbone of 5 to 7 atoms;

wherein said backbone can be substituted by $C_{1-6}$ alkyl, $C_{1-6}$ cycloalkyl, or $C_{6-12}$ aryl;

and comprises at least one rigidifying moiety connected to at least two atoms of the backbone;

said moiety selected from the group consisting of double bond, triple bond, saturated or unsaturated $C_{3-9}$ cycloalkyl, and $C_{6-12}$ aryl.

By the term rigidifying moiety is meant a moiety that will confer rigidity to the hydrophobic tail. The rigidifying moiety connects at least two atoms which are part of the backbone of the hydrophobic tail. For example, the backbone of the following hydrophic tail is as follows:

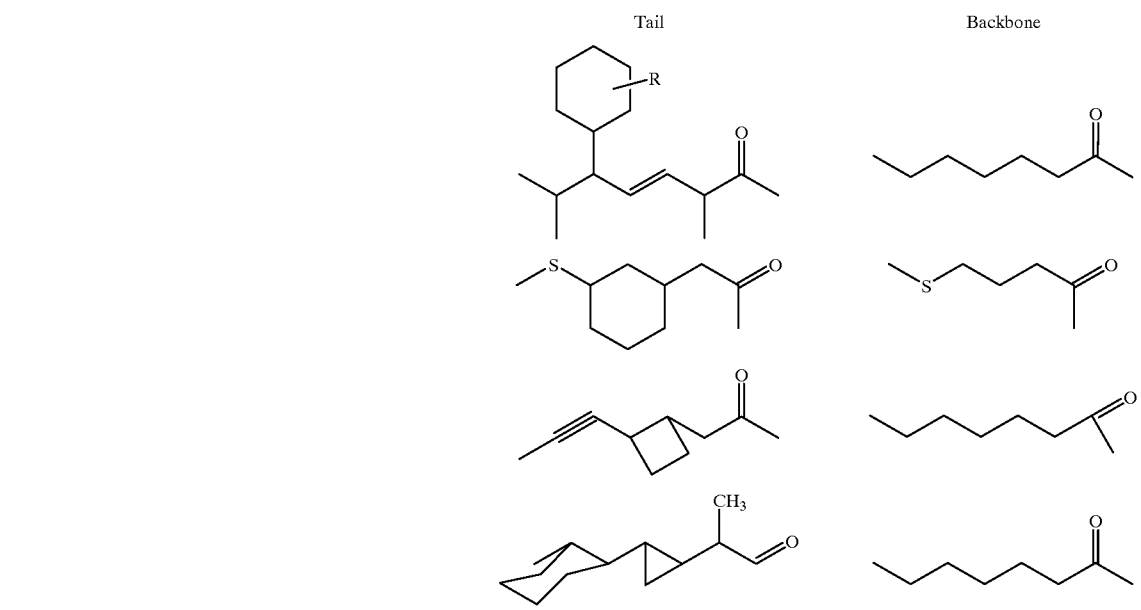

Preferably, the backbone is substituted with 2 rigidifying moieties which are independently selected from the group consisting of double bond and saturated or unsaturated $C_{3-9}$ cycloalkyl.

More preferably, the backbone is substituted with 2 rigidifying moieties which are independently selected from the group consisting of double bond, triple bond, saturated $C_{3-7}$ cycloalkyl and $C_6$ aryl.

In an alternative embodiment, the backbone is substituted with one rigidifying moiety selected from the group consisting of double bond, triple bond, saturated $C_{3-7}$ cycloalkyl and $C_6$ aryl.

In an alternative embodiment, the backbone is substituted one rigidifying moiety selected from the group consisting of double bond, triple bond, saturated $C_{3-7}$ cycloalkyl and $C_6$ aryl, which are located at the 3,4-positions, the 3,5-positions or the 3,6-positions of the backbone.

Preferably, the hydrophobic tail is selected from the group consisting of:

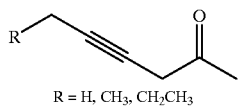

R = H, $CH_3$, $CH_2CH_3$

-continued

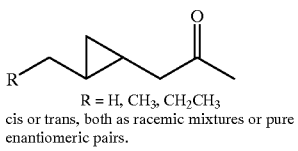

R = H, CH₃, CH₂CH₃
cis or trans, both as racemic mixtures or pure
enantiomeric pairs.

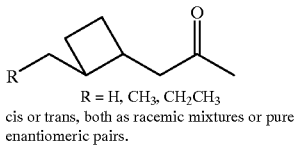

R = H, CH₃, CH₂CH₃
cis or trans, both as racemic mixtures or pure
enantiomeric pairs.

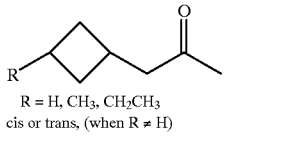

R = H, CH₃, CH₂CH₃
cis or trans, (when R ≠ H)

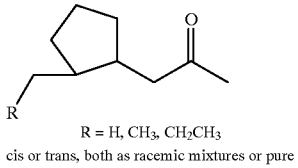

R = H, CH₃, CH₂CH₃
cis or trans, both as racemic mixtures or pure
enantiomeric pairs.

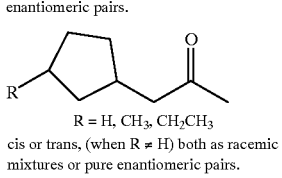

R = H, CH₃, CH₂CH₃
cis or trans, (when R ≠ H) both as racemic
mixtures or pure enantiomeric pairs.

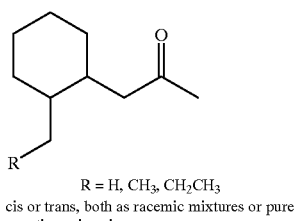

R = H, CH₃, CH₂CH₃
cis or trans, both as racemic mixtures or pure
enantiomeric pairs.

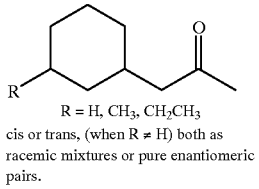

R = H, CH₃, CH₂CH₃
cis or trans, (when R ≠ H) both as
racemic mixtures or pure enantiomeric
pairs.

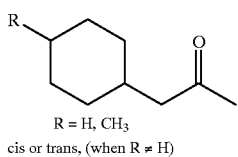

R = H, CH₃
cis or trans, (when R ≠ H)

In accordance with the present invention, there is provided a method of increasing the level of growth hormone in a patient which comprises administering to said patient an effective amount of a GRF analog of the present invention.

In accordance with the present invention, there is provided a method for the diagnosis of growth hormone deficiencies in patients, which comprises administering to said patient a GRF analog of the present invention and measuring the growth hormone response.

In accordance with the present invention, there is provided a method for the treatment of pituitary dwarfism or growth retardation in a patient, which comprises administering to said patient an effective amount of a GRF analog of the present invention.

In accordance with the present invention, there is provided a method for the treatment of wound or bone healing in a patient, which comprises administering to said patient an effective amount of a GRF analog of the present invention.

In accordance with the present invention, there is provided a method for the treatment of osteoporosis in a patient, which comprises administering to said patient an effective amount of a GRF analog of the present invention.

In accordance with the present invention, there is provided a method for improving protein anabolism (including protein sparing effect) in human or animal, which comprises administering to said human or animal an effective amount of a GRF analog of the present invention.

In accordance with the present invention, there is provided a method for inducing a lipolytic effect in human or animal afflicted with clinical obesity, which comprises administering to said human or animal an effective amount of a GRF analog of the present invention.

In accordance with the present invention, there is provided a method for the overall upgrading of somatotroph function in human or animal, which comprises administering to said human or animal an effective amount of a GRF analog of the present invention.

In the present invention the amino acids are identified by the conventional three-letter abbreviations as indicated below, which are as generally accepted in the peptide art as recommended by the IUPAC-IUB commission in biochemical nomenclature:

| | | |
|---|---|---|
| | Alanine | Ala |
| | Arginine | Arg |
| | Asparagine | Asn |
| | Aspartic Acid | Asp |
| | Cysteine | Cys |
| | Glutamic Acid | Glu |
| | Glycine | Gly |
| | Histidine | His |
| | Leucine | Leu |
| | Lysine | Lys |
| | Methionine | Met |
| | Ornithine | Orn |
| | Phenylalanine | Phe |
| | Proline | Pro |
| | Serine | Ser |
| | Threonine | Thr |
| | Tryptophane | Trp |
| | Tyrosine | Tyr |
| | D-Tyrosine | Tyr |
| | Valine | Val |

The term "natural amino acid" means an amino acid which occurs in nature or which is incorporated as an amino acid residue in a naturally occurring peptide. In addition, the abbreviation Nle is intended to mean Norleucine.

Other abbreviations used are:

| | |
|---|---|
| TFA | Trifluoroacetic acid; |
| HOBt | 1-Hydroxybenzotriazole; |
| DIC | Diisopropylcarbodiimide; |
| DMF | Dimethylformamide; |
| Pip | Piperidine; |
| DMAP | 4-dimethylaminopyridine; |
| Boc | t-butyloxycarbonyl; |
| Fmoc | Fluorenylmethyloxycarbonyl; |
| BOP | Benzotriazo-1-yloxytris (dimethylamino) phosphonium hexafluorophosphate; |
| Me | Methyl; |

-continued

| | |
|---|---|
| HF | Hydrofluoric acid; |
| NEt₃ | Triethylamine; and |
| TEAP | Triethylammonium phosphate (buffer). |

All the peptide sequences set out herein are written according to the generally accepted convention whereby the N-terminal amino acid is on the left and the C-terminal amino acid is on the right.

BRIEF DESCRIPTION OF THE DRAWINGS

FIG. 6A to 6C illustrate examples of specific synthesis of GRF analogs with preferred radicals R in accordance with the present invention.

DETAILED DESCRIPTION OF THE INVENTION

Figure 1:
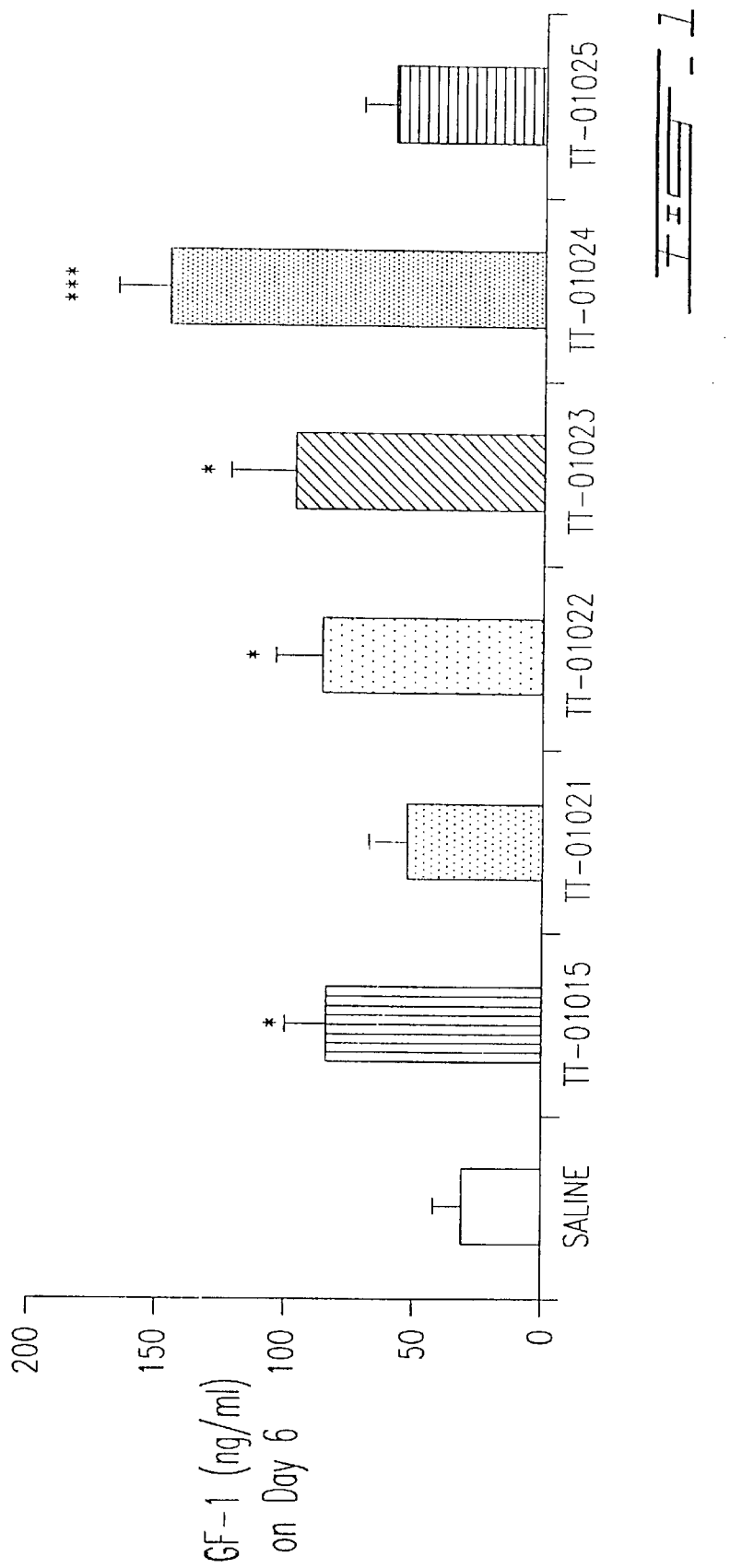
FIG. 1 is a graph of the effect of subcutaneously injected hGRF(1–29)NH$_2$ analogs on pig serum IGF-1.

The present invention relates to the use of fatty bodies, namely pseudomicellar residues and/or hydrophobic tails, to produce a new family of highly potent, chimeric fatty body-GRF analogs.

In accordance with the present invention, the fatty body-GRF analogs can be chemically synthesized by anchoring one or several hydrophobic tails at the C- and/or the N-terminal portion of GRF or one of its analogs.

For a better carrying out of the chemical anchoring reaction, hydrophobic functionalized under the acid form are preferably used. In these conditions, the anchoring reaction is preferably effected in a solid phase (Merrifield R. B., 1963, *J. Am. Chem. Soc.*, 85:2149; 1964, *J. Am. Chem. Soc.*, 86:304) using extremely active reagents such as for example Benzotriazole-1-yloxytris (dimethylamino) phosphonium hexafluoro-phosphate known in the prior art (B. Castro et al., 1975, *Tetrahedron letters*, Vol. 14:1219).

In the case where the hydrophobic tail to be anchored consists in a fatty acid, the activation in view of the anchoring may be carried out in si tu. Depending on the synthesis strategies used, the peptide anchoring site is liberated just prior to the anchoring in traditional deprotection conditions (Gross et Meienhofer, 1981, The peptides, vol. 3, Academic press: pages 1–341). The hydrophobic tail (Ht) is then condensed with the anchoring agent in organic solvents such as an ether (tetrahydrofuranne), an aliphatic halogenated solvent (dichloromethane), a nitrile (acetonitrile) or an amide (dimethylformamide).

With respect to the anchoring dynamic, the preferred working temperatures are between 20 and 60° C. The anchoring reaction time when hydrophobic tail used are more and more hydrophobic, varies inversely with temperature, but varies between 0.1 and 24 hours.

As an illustrative example, the triacyl lysine synthesis as set forth below illustrates in a schematic manner the whole of the anchoring principle of a hydrophobic fatty acid tail.

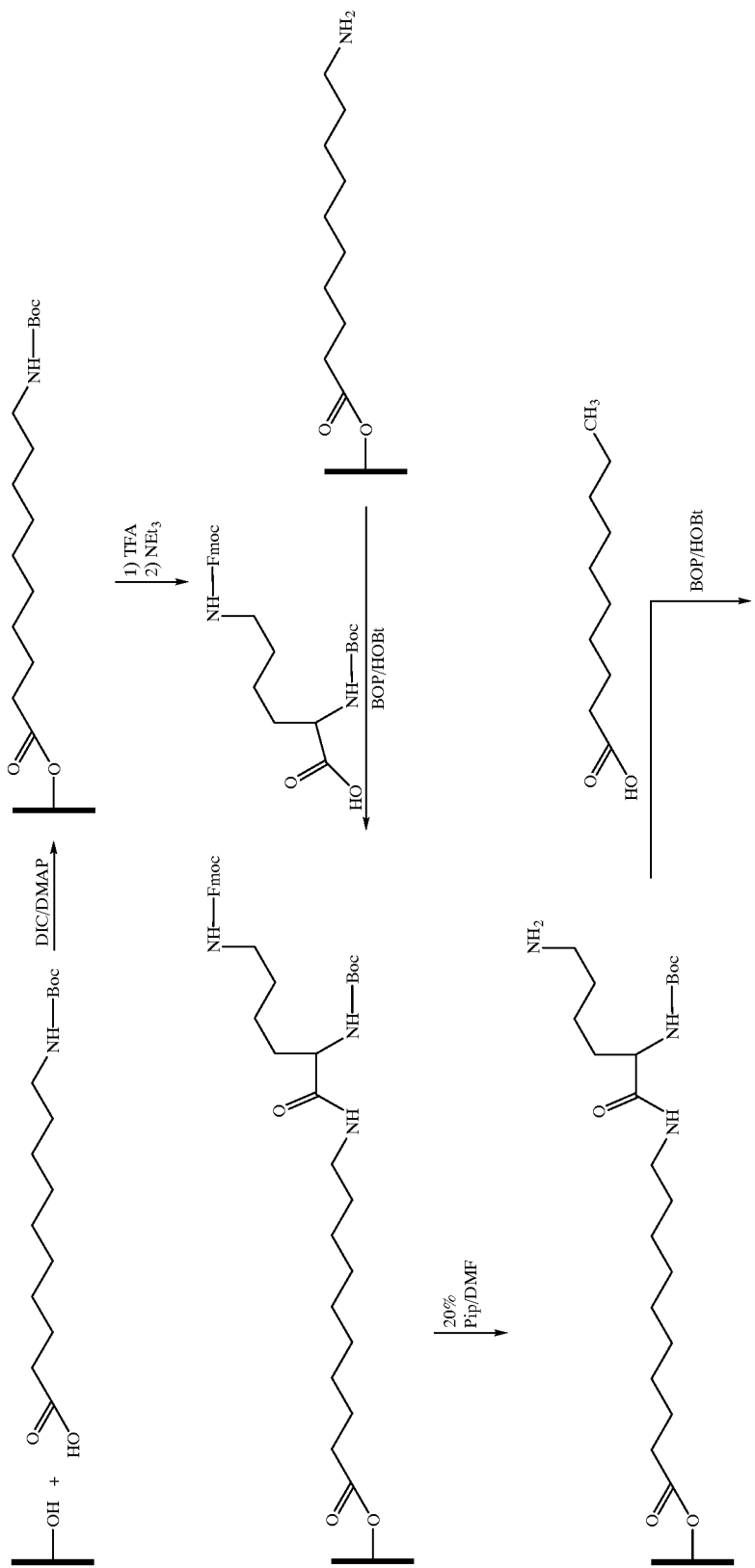

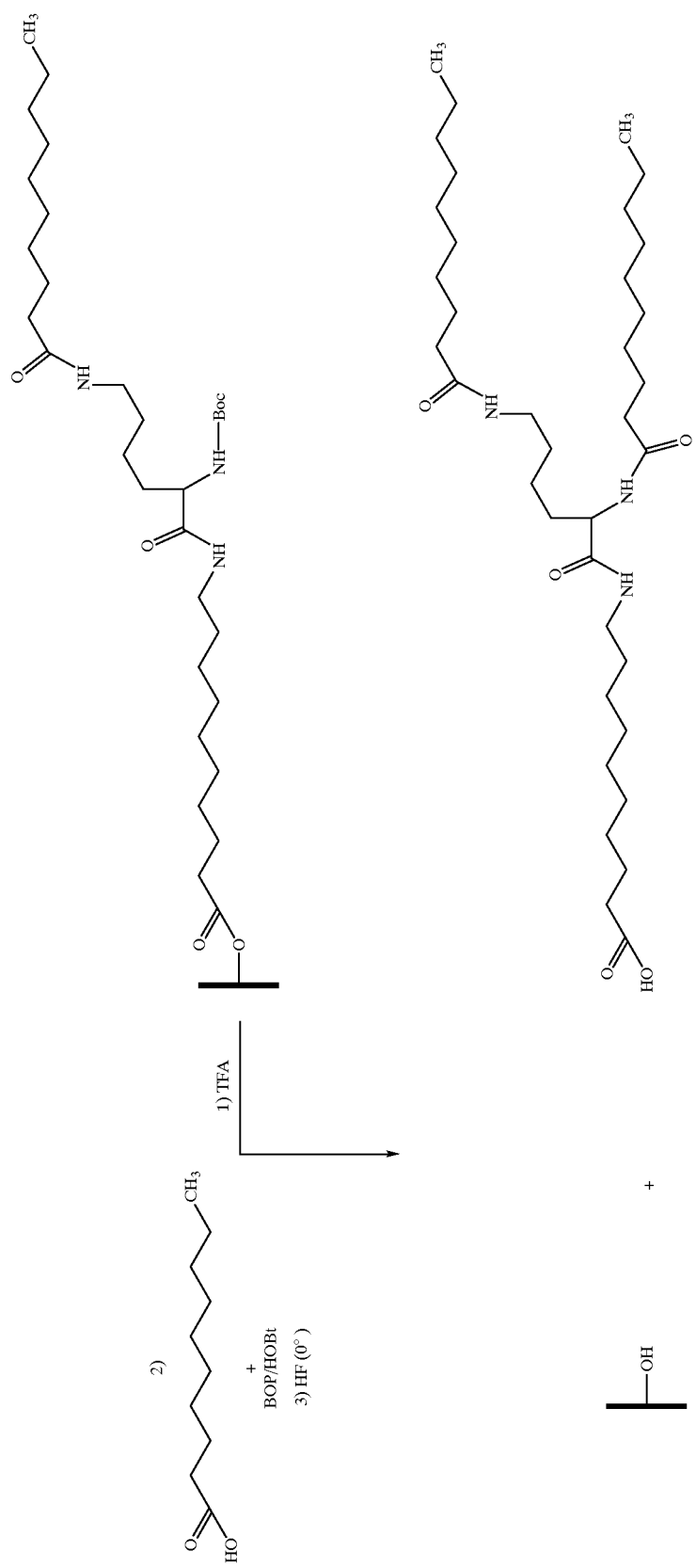

General GRF analogs synthesis steps were carried out by solid-phase methodology on a 9050™ plus peptide synthesizer (Millipore Corporation, Milford, Mass.) using Fmoc strategy and synthesis cycles supplied by Millipore. Fmoc amino acids were supplied by Bachem California and other commercials sources. Sequential Fmoc chemistry using BOP/HOBt as coupling methodology were applied to the starting Fmoc-Pal-PEG resin (Millipore, catalog number: GEN 913383) for the production of C-terminal carboxamides. Fmoc deprotections were accomplished with piperidine 20% solution in DMF. After synthesis completion, the resin was well washed with DMF and ether prior to drying. Final cleavages of side chain protecting groups and peptide-resin bonds were performed using Millipore supplied procedure consisting of the following mixture: TFA, water, phenol, triisopropylsilane (88:5:5:2). Peptides were then precipitated and washed with ether prior to drying. Reverse phase HPLC purification (buffer A: TEAP 2.5; buffer B: 80% $CH_3CN$ in A) using a water pep 4000, absorbance 214 nm, detector model 486, flow rate 50 ml/min.; linear gradient generally from 25 to 60%B in 105 min.) followed by a desalting step (buffer C:0.1% TFA in $H_2O$; buffer D:0.1% TFA in $CH_3CH/H_2O$ 80:20) afforded peptides in yields amounting from 10 to 30% with homogeneity greater than 97% as estimated by HPLC (millennium/photodiode array detection).

In accordance with the present invention, the pig was selected as a test specie, since it is a valuable preclinical model for the development of GRF analogs. Indeed, human and porcine $GRF(1-29)NH_2$ share a 100% homology of structure, and the physiological pattern of GH secretion is almost identical in both species.

Moreover, the potency of the GRF analogs was assessed as their ability to significantly increase IGF-I blood levels rather than their acute GH releasing potency. Indeed, it is known that the anabolic and healing effects of GH or GRF induced GH are mediated by an increase in IGF-I synthesis and secretion. Therefore, the measurement of GRF induced IGF-I elevation is the best indicator of the treatment efficacy.

The present invention will be more readily understood by referring to the following examples which are given to illustrate the invention rather than to limit its scope.

EXAMPLE I

Effect of Repeated Administrations of [BUTYRYL$^0$], [OCTANOYL$^0$]-, [HEXANOYL$^0$]- [HEXANOYL$^{30}$], [HEXANOYL$^{0,30}$], HGRF(1–29) $NH_2$ and [HEXANOYL$^0$] HGRF(1–44)$NH_2$ VS hGRF(1–29)$NH_2$ on Serum IGF-I Levels in Pigs The objective of these experiments was to assess the potential of the GRF analogs as anabolic agents. It is known that GH or GRF-induced GH secretion exert their anabolic effect via an increase in insulin-like growth factor I (IGF-I) synthesis and secretion, that result in elevated levels of circulating IGF-I. It has been previously demonstrated that the intensity of the anabolic response to a GRF analog treatment is proportional to the increase in IGF-I levels in pigs (Dubreuil P. et al., 1990, *J. Anim. Sci.*, 68:1254–1268).

Therefore, in order to investigate the anabolic potency of the fatty acid-GRF analogs, their ability to increase IGF-I levels following repeated S.C. administrations in pig was evaluated.

Experiment 1

26 Landrace×Yorkshire castrated male pigs (40–45 kg BW) were randomly distributed into 4 experimental groups:

1—hGRF(1–29)$NH_2$ (20 μg/kg, n=7)
2—[octanoyl$^0$] hGRF(1–29)$NH_2$ (20 μg/kg, n=6)
3—[hexanoyl$^0$] hGRF(1–29)$NH_2$ (20 μg/kg, n=6)
4-[butyryl$^0$] hGRF(1–29)$NH_2$ (20 μg/kg, n=7)

Each animal was injected BID (twice a day) subcutaneously for 4 consecutive days. One blood sample was collected each morning prior to the first injection of the day, and the day after the last injection, for IGF-I measurement.

Experiment 2

40 Landrace×Yorkshire castrated male pigs (40–45 kg BW) were randomly distributed into 5 experimental groups:

1—saline (n=8)
2—hGRF(1–29)$NH_2$ (40 μg/kg, n=8)
3—[hexanoyl$^0$] hGRF(1–29)$NH_2$ (10 μg/kg, n=8)
4—[hexanoyl$^0$] hGRF(1–29)$NH_2$ (20 μg/kg, n=8)
5—[hexanoyl$^0$] hGRF(1–29)$NH_2$ (40 μg/kg, n=8)

Each animal was injected BID (twice a day) subcutaneously for 5 consecutive days. One blood sample was collected each morning prior to the first injection of the day, and the day after the last injection, for IGF-I measurement.

Experiment 3

48 Landrace×Yorkshire castrated male pigs (40–45 kg BW) were randomly distributed into 6 experimental groups:

1—Saline (n=8)
2—hGRF(1–44)$NH_2$ (30 μg/kg, n=8)
3—[hexanoyl$^0$]hGRF(1–44)$NH_2$ (30 μg/kg, n=8)
4—[hexanoyl$^0$]hGRF(1–29)$NH_2$ (20 μg/kg, n=8)
5—[hexanoyl$^{30}$]hGRF(1–29)$NH_2$ (20 μg/kg, n=8)
6—[hexanoyl$^{0,30}$]hGRF(1–29)$NH_2$ (20 μg/kg, n=8)

The selected doses were 30 μg/kg for hGRF(1–44)$NH_2$ analogs and 20 μg/kg for hGRF(1–29)$NH_2$ analogs, which give identical doses on a molar basis. Each animal was injected BID (twice a day) subcutaneously for 5 consecutive days. One blood sample was collected each morning prior to the first injection of the day, and the day after the last injection, for IGF-I measurements.

IGF-I Measurements

IGF-I levels were measured in pig serum by double antibody radioimmunoassay after formic acid-acetone extraction, as previously described (Abribat T. et al., 1993, *J. Endocrinol.*, 39:583–589). The extraction prior to radioimmunoassay is a necessary step to remove endogenous IGF-binding proteins.

Statistical Analysis

In both experiments, the IGF-I data were analyzed by a two way repeated measure analysis of variance, with day and treatment (GRF analog) as sources of variation. Multiple comparison procedures were there run (Student-Newman Keuls method). A P<0.05 was considered as statistically significant.

Results

Experiment 1

There were both a significant effect of day (P=0.0004) and a significant treatment×day interaction (P=0.011), indicating that the increase in IGF-I levels was dependent on the analog tested (Table 1). Blood samples for IGF-I measurements were collected daily prior to the first injection of compounds. Data are shown as mean±SEM of 6 to 7 values per group.

TABLE 1

Effect of repeated SC injection (20 μg/kg BID × 4 days) of GRF analogs on serum IGF-I levels

| Treatment (BID, 20 μg/kg SC) | Day 1 (pretreatment) (ng/ml) | Day 2 (ng/ml) | Day 3 (ng/ml) | Day 4 (ng/ml) | Day 5 (ng/ml) |
|---|---|---|---|---|---|
| hGRF(1–29)NH$_2$ | 252 ± 28 | 235 ± 19 | 263 ± 16 | 258 ± 17 | 262 ± 24 |
| [octanoyl$^0$] hGRF(1–29)NH$_2$ | 316 ± 22 | 287 ± 20 | 301 ± 37 | 301 ± 37 | 318 ± 39 |
| [hexanoyl$^0$] hGRF(1–29)NH$_2$ | 248 ± 20 | 281 ± 28 | 299 ± 26 | 319 ± 22$^a$ | 342 ± 21$^{a,b}$ |
| [butyril$^0$] hGRF(1–29)NH$_2$ | 278 ± 20 | 281 ± 24 | 302 ± 26 | 289 ± 26 | 293 ± 23 |

Treatment P = 0.42
Day P = 0.0004
Treatment × Day P = 0.011
$^a$P < 0.05 when compared to day 1
$^b$P < 0.05 when compared to day 2

Multiple comparisons revealed that only [hexanoyl$^0$] hGRF(1–29)NH$_2$ elicited an increase in IGF-I levels, which was significant on days 4 (29%, P<0.05) and 5 (38%, P<0.05). Human GRF(1–29)NH$_2$ had no effect on IGF-I levels at the dose tested.

Experiment 2

There were both a significant effect of day (P<0.0001) and a significant treatment×day interaction (P<0.0001), indicating that the increase in IGF-I levels was dependent on the analog tested (Table 2). Blood samples for IGF-I measurements were collected daily prior to the first injection of the day. Data are shown as mean±SEM of 8 values per group.

TABLE 2

Dose-related effect of repeated SC injection (BID × 5 days) of GRF analogs on serum IGF-I levels

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
|---|---|---|---|---|---|---|
| saline | 282 ± 33 | 266 ± 30 | 281 ± 34 | 293 ± 30 | 287 ± 32 | 289 ± 33 |
| hGRF(1-29)NH$_2$ (40 μg/kg) | 244 ± 24 | 243 ± 16 | 267 ± 20 | 275 ± 27 | 267 ± 17 | 256 ± 15 |
| [hexanoyl$^0$] hGRF (1-29)NH$_2$ (10 μg/kg) | 303 ± 31 | 327 ± 20 | 337 ± 25 | 338 ± 25 | 366 ± 37$^a$ | 350 ± 34$^a$ |
| [hexanoyl$^0$] hGRF (1-29)NH$_2$ (20 μg/kg) | 302 ± 38 | 341 ± 37 | 368 ± 43$^a$ | 362 ± 40$^a$ | 362 ± 45$^a$ | 368 ± 57$^a$ |
| [hexanoyl$^0$] hGRF (1-29)NH$_2$ (40 μg/kg) | 252 ± 35 | 275 ± 32 | 319 ± 31$^a$ | 354 ± 41$^{a,b}$ | 350 ± 34$^{a,b}$ | 374 ± 33$^{a,b,c}$ |

Treatment P = 0.23; Day P = 0.0001
Treatment × Day P = 0.0001
$^a$P < 0.05 when compared to day 1
$^b$P < 0.05 when compared to day 2
$^c$P < 0.05 when compared to day 3

Multiple comparisons revealed that all three tested doses of [hexanoyl$^0$] hGRF(1–29)NH$_2$ increased IGF-I levels. At 10 μg/kg, IGF-I levels were significantly increased at days 5 and 6 (16 to 21%, P<0.05). At 20 μg/kg, they were increased at days 3, 4, 5 and 6 (20 to 22%, P<0.05). At 40 μg/kg, they were increased at days 3, 4, 5 and 6 (27 to 48%, P<0.05). The serum IGF-I levels remained stable in saline— and hGRF(1–29)NH$_2$—treated pigs.

Finally, a regression analysis revealed that the increase in IGF-I concentrations from day 1 to day 6 was dependent on the dose of [hexanoyl$^0$] hGRF(1–29)NH$_2$ (ΔIGF-I=11.9+ (2.77*dose); r=0.68, P<0.0001).

Experiment 3

There were both a significant effect of day (P<0.0001) and a significant treatment×day interaction (P<0.0001), indicating that the increase in IGF-I levels was dependent on the analog tested (Table IV). Multiple comparison revealed that analogs with an hexanoyl function branched at the N-terminal region of GRF were highly potent:

[hexanoyl$^0$] hGRF(1–29)NH$_2$ significantly increased IGF-I levels on days 5 and 6 (by 28% and 31%, P<0.05)

[hexanoyl$^{0, 30}$] hGRF(1–29)NH$_2$ significantly increased IGF-I levels on days 4, 5 and 6 (by 32%, 35% and 43%, P<0.05)

[hexanoyl$^0$] hGRF(1–44)NH$_2$ significantly increased IGF-I levels on days 3, 4, 5 and 6 (by 41%, 54%, 50% and 61%, P<0.05)

As previously observed for hGRF(1–29)NH$_2$ (experiments 1 and 2), the full length hGRF(1–44)NH$_2$ had little or no effect on IGF-I levels (except for a significant effect on day 5, which was not sustained on day 6). Finally, the anchoring of an hexanoyl function at the C-terminal region of hGRF(1–29)NH$_2$ yielded an analog with increased potency when compared to hGRF(1–29)NH$_2$ (21% increased in IGF-I levels on day 6, P<0.05), but less potent than [hexanoyl$^0$]hGRF(1–29)NH$_2$.

Human GRF(1–29)NH$_2$ and hGRF(1–44)NH$_2$ were injected at 20 μg/kg and 30 μg/kg, respectively, in order to achieve equimolar concentrations. Data shown are mean±SEM of 8 values per group.

TABLE 3

Effect of multiple SC injections of GRF analogs (BID x 5 days) on serum IGF-I levels in growing pigs

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
|---|---|---|---|---|---|---|
| saline | 215 ± 21 | 215 ± 28 | 219 ± 25 | 226 ± 28 | 249 ± 30 | 234 ± 24 |
| hGRF(1-44)NH$_2$ (30 µg/kg) | 245 ± 21 | 254 ± 22 | 285 ± 26 | 297 ± 28 | 303 ± 26$^a$ | 296 ± 26 |
| [hexanoyl$^0$] hGRF (1-29)NH$_2$ (20 µg/kg) | 272 ± 45 | 292 ± 52 | 292 ± 57 | 315 ± 57 | 347 ± 44$^{a,b,c}$ | 356 ± 44$^{a,b,c}$ |
| [hexanoyl$^{30}$] hGRF (1-29)NH$_2$ (20 µg/kg) | 297 ± 30 | 270 ± 25 | 287 ± 24 | 278 ± 18 | 276 ± 20 | 327 ± 24$^b$ |
| [hexanoyl$^{0,30}$] hGRF (1-29)NH$_2$ (20 µg/kg) | 205 ± 24 | 212 ± 26 | 253 ± 33 | 271 ± 36$^{a,b}$ | 277 ± 29$^{a,b}$ | 294 ± 26$^{a,b}$ |
| [hexanoyl$^0$] hGRF (1-44)NH$_2$ (30 µg/kg) | 241 ± 30 | 290 ± 33 | 340 ± 41$^a$ | 372 ± 40$^{a,b}$ | 361 ± 46$^{a,b}$ | 388 ± 49$^{a,b,c}$ |

Treatment P = 0.16
Day P < 0.0001
Treatment x Day P < 0.0001
$^a$P < 0.05 when compared to day 1
$^b$P < 0.05 when compared to day 2
$^c$P < 0.05 when compared to day 3

Conclusions

Neither hGRF(1–29)NH$_2$ nor hGRF(1–44)NH$_2$ at doses ranging from 20 to 40 µg/kg were able to modulate IGF-I levels. However, the anchoring of fatty acid rendered GRF more potent and yielded analogs with markedly improved activity on IGF-I secretion. The anchoring of fatty acids was efficient in improving the anabolic potency of both hGRF (1–29)NH$_2$ and hGRF(1–44)NH$_2$. From the above results, it is concluded that the ideal fatty acid to use is hexanoic acid or any C6 fatty derivative, and that it should be preferably anchored at the N-terminal region of GRF to yield maximally potent analogs.

EXAMPLE II

Comparative Effects of GRF Analogs on IGF-I Levels in Pigs

This was a 5-day treatment, twice a day S.C. administration of one single dose of each test article vs saline. This experiment was conducted to compare the efficacy of (Aminohexanoyl)$_0$ hGRF (1–29) NH$_2$, (Hexylformiate)$_0$ hGRF (1–29) NH$_2$, (Hexenoyl trans-2)$_0$ hGRF (1–29) NH$_2$, (Hexenoyl trans-3)$_0$ hGRF (1–29) NH$_2$ and (Muconoyl)$_0$ hGRF (1–29) NH$_2$ to that of (Hexanoyl)$_0$ hGRF (1–29) NH$_2$.

All tested compounds belong to the same family of GRF analogs: they are a combination of the natural GRF and natural fatty acids, designed to improve the activity of the molecule.

| | Identity of tested analogs: | in saline |
|---|---|---|
| TT-01015 | (Hexanoyl)$_0$ hGRF (1–29) NH$_2$ | 20 µg/kg |
| TT-01021 | (Aminohexanoyl)$_0$ hGRF (1–29) NH$_2$ | 20 µg/kg |
| TT-01022 | (Hexylformiate)$_0$ hGRF (1–29) NH$_2$ | 20 µg/kg |
| TT-01023 | (Hexenoyl trans-2)$_0$ hGRF (1–29) NH$_2$ | 20 µg/kg |
| TT-01024 | (Hexenoyl trans-3)$_0$ hGRF (1–29) NH$_2$ | 20 µg/kg |
| TT-01025 | (Muconoyl)$_0$ hGRF (1–29) NH$_2$ | 20 µg/kg |

Route and Frequency of Test Article
ADMINISTRATION: Two daily subcutaneous injections.
TEST SYSTEM: Landrace×Yorkshire pigs.
ANIMAL DESCRIPTION: Fifty six (56) growing barrows pigs weighing 35 kg at the time of purchase.
RATION: Commercial feed concentrate (18% protein) offered ad libitum.
EXPERIMENTAL DESIGN: Fifty six (56) pigs were randomly distributed into 7 experimental groups (n=8 pigs per group). Each group received two daily S.C. administration of the following treatments (volume: 3 ml, S.C. injection).

group 1: saline 2×/day
group 2: TT-01015 20 µg/kg 2×/day
group 3: TT-01021 20 µg/kg 2×/day
group 4: TT-01022 20 µg/kg 2×/day
group 5: TT-01023 20 µg/kg 2×/day
group 6: TT-01024 20 µg/kg 2×/day
group 7: TT-01025 20 µg/kg 2×/day Treatments were administered from day 1 to 5. Immediately before the injections, one blood sample were collected from each animal, and additional blood samples were collected on day 6.

Blood samples were allowed to clot, serum was harvested by centrifugation and submitted to IGF-I assays.

Results are shown in FIG. 1 as D-IGF-I, which is defined as the increase in IGF-I levels from day 1 (pretreatment levels) to day 6 (after 5 days of GRFs administrations). Among all analog tested, only hexanoyl-, hexylformiate-, hexenoyl trans2- and hexenoyl trans3-hGRF(1–29)NH$_2$ significantly increased IGF-I levels over the 6-day study period, whereas aminohexanoyl- and muconoyl-hGRF (1–29)NH$_2$ did not. Since hGRF(1–29)NH$_2$ has been shown to be ineffective at the same dose in the same conditions in previous assays (see Example I), these results show that the addition of various C6 carbon chains at the N-terminus region of GRF increases its bioactivity.

EXAMPLE III

Intravenous GH-releasing Potency of (Hexenoyl trans-3)$_0$ hGRF (1–29) NH2 vs hGRF(1–29)NH$_2$ in Pigs This experiment was conducted to test the I.V. acute GH-releasing potency of (Hexenoyl trans-3)$_0$ hGRF (1–29)

NH$_2$, a GRF analog, in a model physiologically close to human and to compare it to that of hGRF(1–29)NH$_2$.

(Hexenoyl trans-3)$_0$ hGRF (1–29) NH$_2$ is a combination of the natural hGRF(1–29)NH$_2$ and natural fatty acids. This study was a multidose, single I.V. injection study.

Identity of Tested Analogs:

| | |
|---|---|
| TT-01024 (Hexenoyl trans-3)$_0$ hGRF (1–29) NH$_2$ | 0.25 µg/kg |
| TT-01024 (Hexenoyl trans-3)$_0$ hGRF (1–29) NH$_2$ | 1 µg/kg |
| TT-01024 (Hexenoyl trans-3)$_0$ hGRF (1–29) NH$_2$ | 4 µg/kg |
| hGRF (1–29)NH$_2$ | 0.25 µg/kg |
| hGRF (1–29)NH$_2$ | 1 µg/kg |
| hGRF (1–29)NH$_2$ | 4 µg/kg |

Route and Frequency of Test Article
ADMINISTRATION: intravenous acute injection.
TEST SYSTEM: Landrace×Yorkshire pigs.
ANIMAL DESCRIPTION: Fifty six (56) growing barrows pigs weighing 35 kg at the time of purchase.
RATION: Commercial feed concentrate (18% protein) offered ad libitum.
EXPERIMENTAL DESIGN: Fifty (56) pigs (4 spare animals) were cannulated (a catheter surgically implanted in one jugular vein) within on week, before the study. On days 1 and 7, cannulated animals were randomly distributed into 7 groups (n=4 pigs per group).

| | |
|---|---|
| group 1: saline | |
| group 2: TT-01024 | 0.25 µg/kg |
| group 3: TT-01024 | 1 µg/kg |
| group 4: TT-01024 | 4 µg/kg |
| group 5: hGRF(1–29)NH$_2$ | 0.25 µg/kg |
| group 6: hGRF(1–29)NH$_2$ | 1 µg/kg |
| group 7: hGRF(1–29)NH$_2$ | 4 µg/kg |

Blood samples for pGH assay were collected every 20 min from 1 hour before to 5 hours after GRF injections, with additional samplings 10 and 30 min after injection (n=21 samples). Blood samples are allowed to clot at +4° C. Serum will be harvested by centrifugation, stored at −20° C. and submitted to pGH assays.

Figure 2:
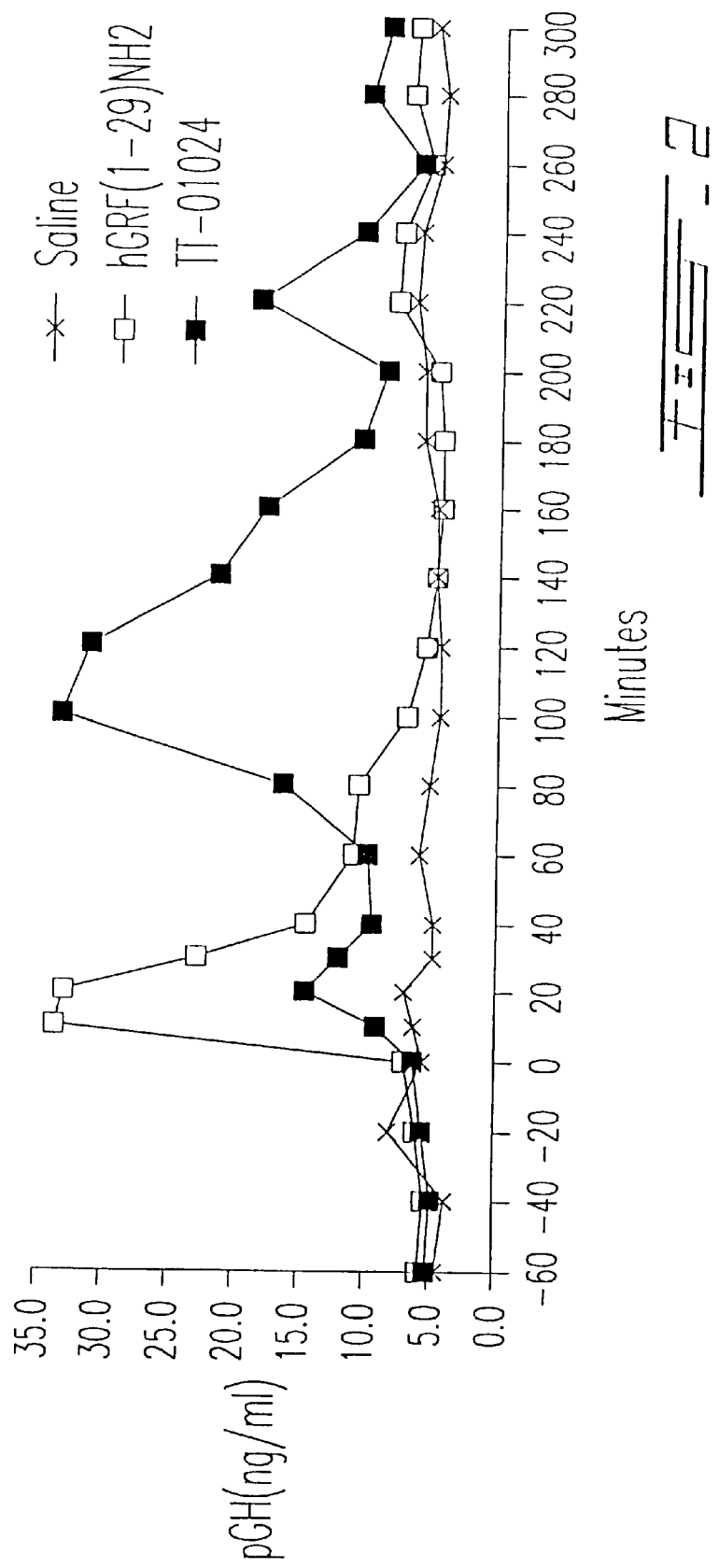
FIG. 2 is a curve of the effect of one intravenous injection of (4 μg/kg) hGRF(1–29)NH$_2$ and (4 μg/kg) (Hexenoyl trans-3)° hGRF (1–29)NH$_2$ (TT-01024)+analog on pig serum GH.
Figure 3:
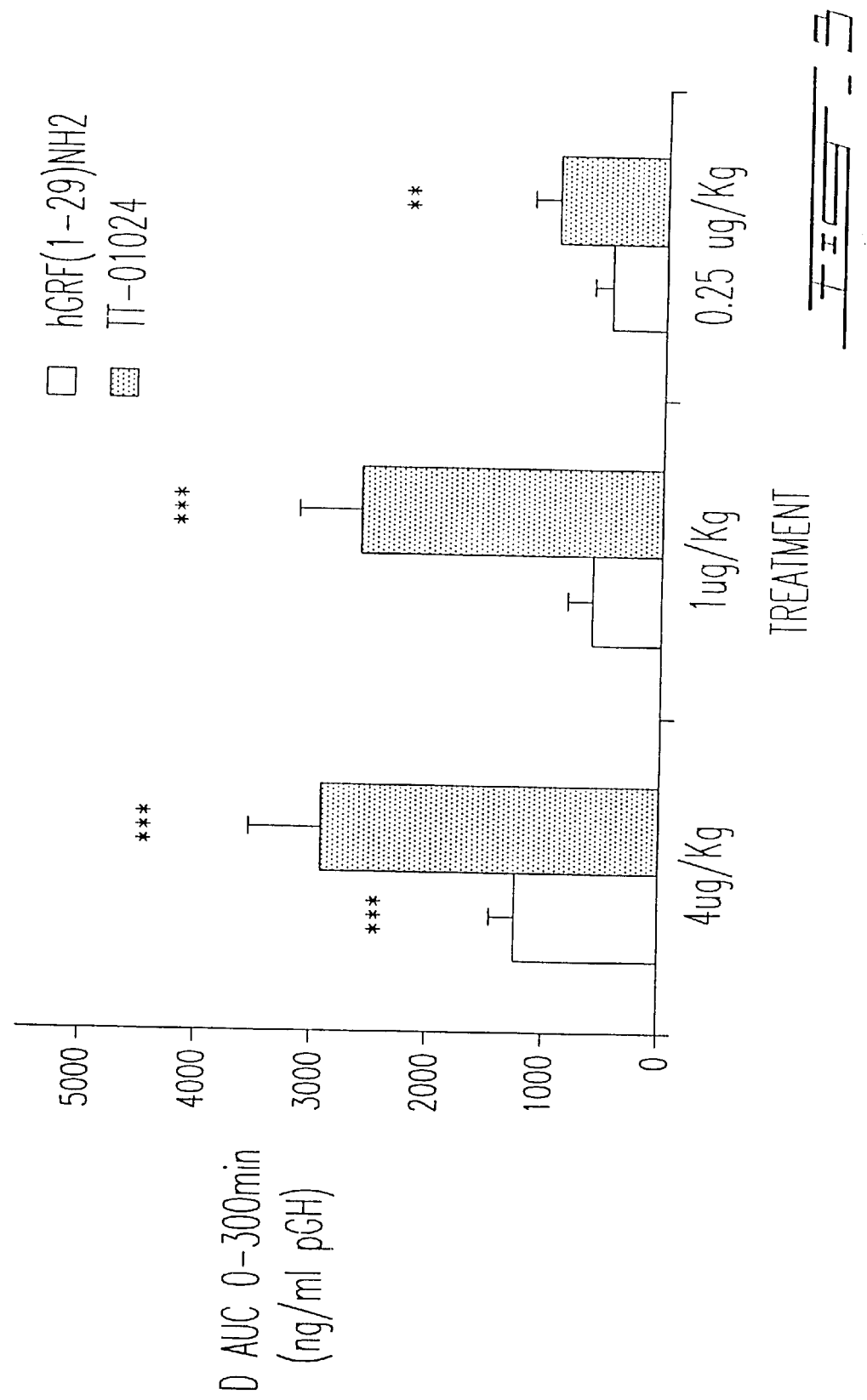
FIG. 3 is a graph showing the effect of various doses of hGRF(1–29)NH$_2$ vs [hexenoyl trans-3]° hGRF(1–29)NH$_2$ (TT-01024) on the GH area under the curve over 300 minutes following I.V. administration (P<0.01 and *P<0.001 when compared to the basal period–60 to 0 min)

Results are illustrated in FIGS. 2 and 3. As shown in FIG. 2, hGRF(1–29)NH$_2$ (4 µg/kg) induced a rapid GH release that was sustained for approximately 60 minutes following injection. In contrast, hexenoyl trans3-hGRF(1–29)NH$_2$ injected at the same dose increased GH levels over a longer period, approximately 260 minutes. In addition, the GH response in the first 60 minutes was moderate, suggesting that this analog acts as a GRF, being processed in serum into native GRF in the minutes or hours following injection. As shown in FIG. 3, which presents the effects of various doses of GRF and the analog on the GH area under the curve (0 to 300 minutes following injection), hGRF(1–29)NH$_2$ produced a significant effect on GH secretion at 4 µg/kg, but not at 0.25 or 1 µg/kg, whereas hexenoyl trans3-hGRF(1–29) NH$_2$ elicited a significant response at all 3 doses tested. In conclusion, these results show that hexenoyl trans3-hGRF (1–29)NH$_2$ is a GRF analog with increased potency on GH secretion, and suggest that it may act as a GRF, being protected from enzymatic degradation in serum.

EXAMPLE IV

Subcutaneous GH-releasing Potency of (Hexenoyl trans-3)$_0$ hGRF (1–29) NH2 vs hGRF(1–29)NH$_2$ in Pigs This experiment was conducted to test the S.C. acute GH-releasing potency of (Hexenoyl trans-3)$_0$ hGRF (1–29) NH$_2$, a GRF analog, in a model physiologically close to human and to compare it to that of hGRF(1–29)NH$_2$.

Identity of tested analogs:
TT-01024 (Hexenoyl trans-3)$_0$ hGRF (1–29) NH$_2$ 0.31 µg/kg
TT-01024 (Hexenoyl trans-3)$_0$ hGRF (1–29) NH$_2$ 1.25 µg/kg
TT-01024 (Hexenoyl trans-3)$_0$ hGRF (1–29) NH$_2$ 5 µg/kg
TT-01024 (Hexenoyl trans-3)$_0$ hGRF (1–29) NH$_2$ 20 µg/kg

| | |
|---|---|
| hGRF (1–29)NH$_2$ | 1.25 µg/kg |
| hGRF (1–29)NH$_2$ | 5 µg/kg |
| hGRF (1–29)NH$_2$ | 20 µg/kg |

Route and Frequency of Test Article
ADMINISTRATION: Subcutaneous acute injection.
TEST SYSTEM: Landrace×Yorkshire pigs.
ANIMAL DESCRIPTION: Sixty four (64) growing barrows pigs weighing 35 kg at the time of purchase.
RATION: Commercial feed concentrate (18% protein) offered ad libitum.
EXPERIMENTAL DESIGN: Thirty six (36) pigs (4 spare animals) were cannulated (a catheter surgically implanted in one jugular vein) within one week, before the study. On days 1 and 7, cannulated animals were randomly distributed into 8 groups (n=4 pigs per group).

| | |
|---|---|
| group 1: saline | |
| group 2: TT-01024 | 0.31 µg/kg |
| group 3: TT-01024 | 1.25 µg/kg |
| group 4: TT-01024 | 5 µg/kg |
| group 5: TT-01024 | 20 µg/kg |
| group 6: hGRF(1–29)NH$_2$ | 1.25 µg/kg |
| group 7: hGRF(1–29)NH$_2$ | 5 µg/kg |
| group 8: hGRF(1–29)NH$_2$ | 20 µg/kg |

Blood samples for pGH assay were collected every 20 min from 1 hour before to 7 hours after GRF injections, (n=25 samples). Blood samples were allowed to clot at +4CC. Serum is harvested by centrifugation, stored at −20° C. and submitted to pGH assays.

Figure 4:
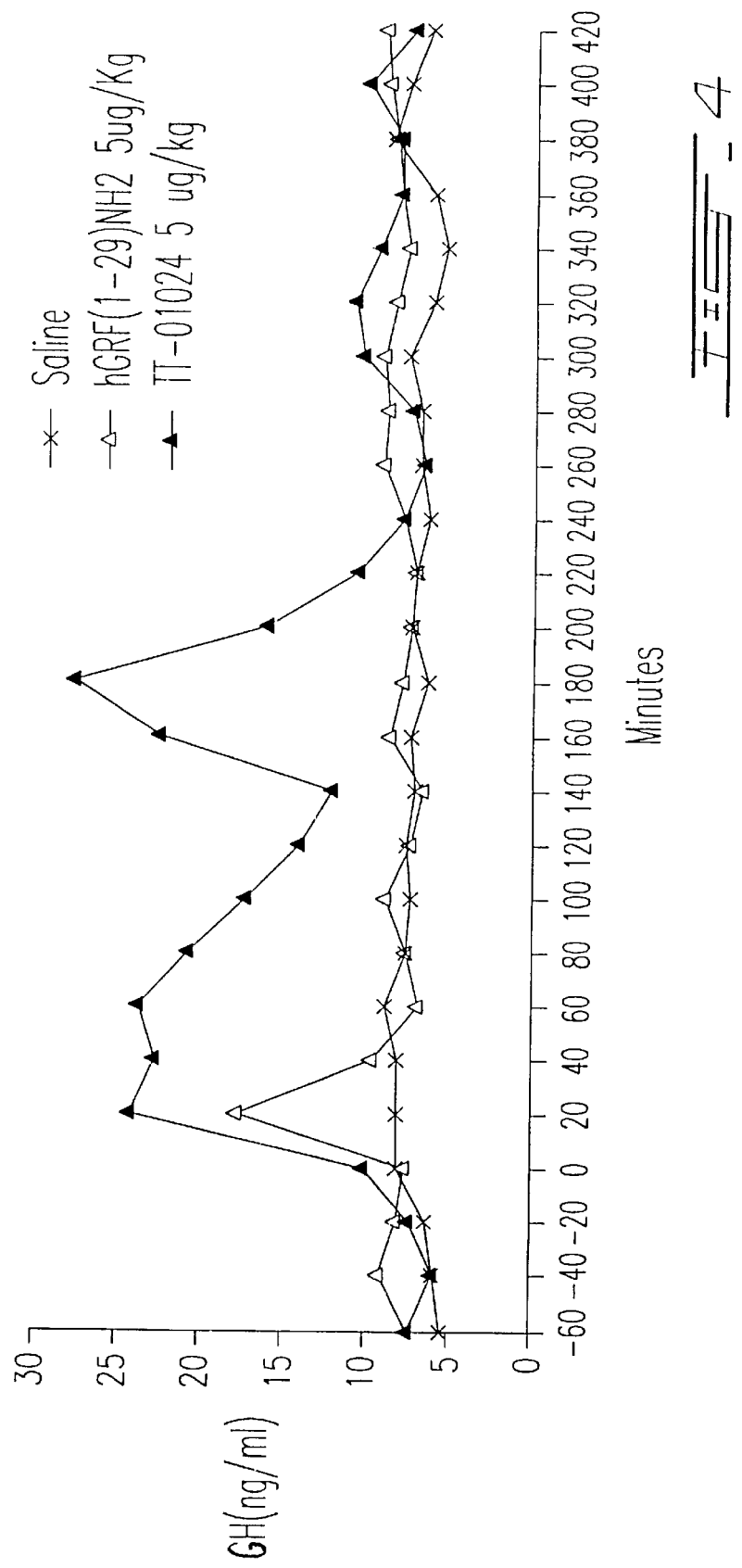
FIG. 4 is a curve of the effect of one subcutaneous injection of 5 μg/kg hGRF(1–29)NH$_2$ and (5 μg/kg) (Hexenoyl trans-3)° hGRF (1–29)NH$_2$ analog on pig serum GH.
Figure 5:
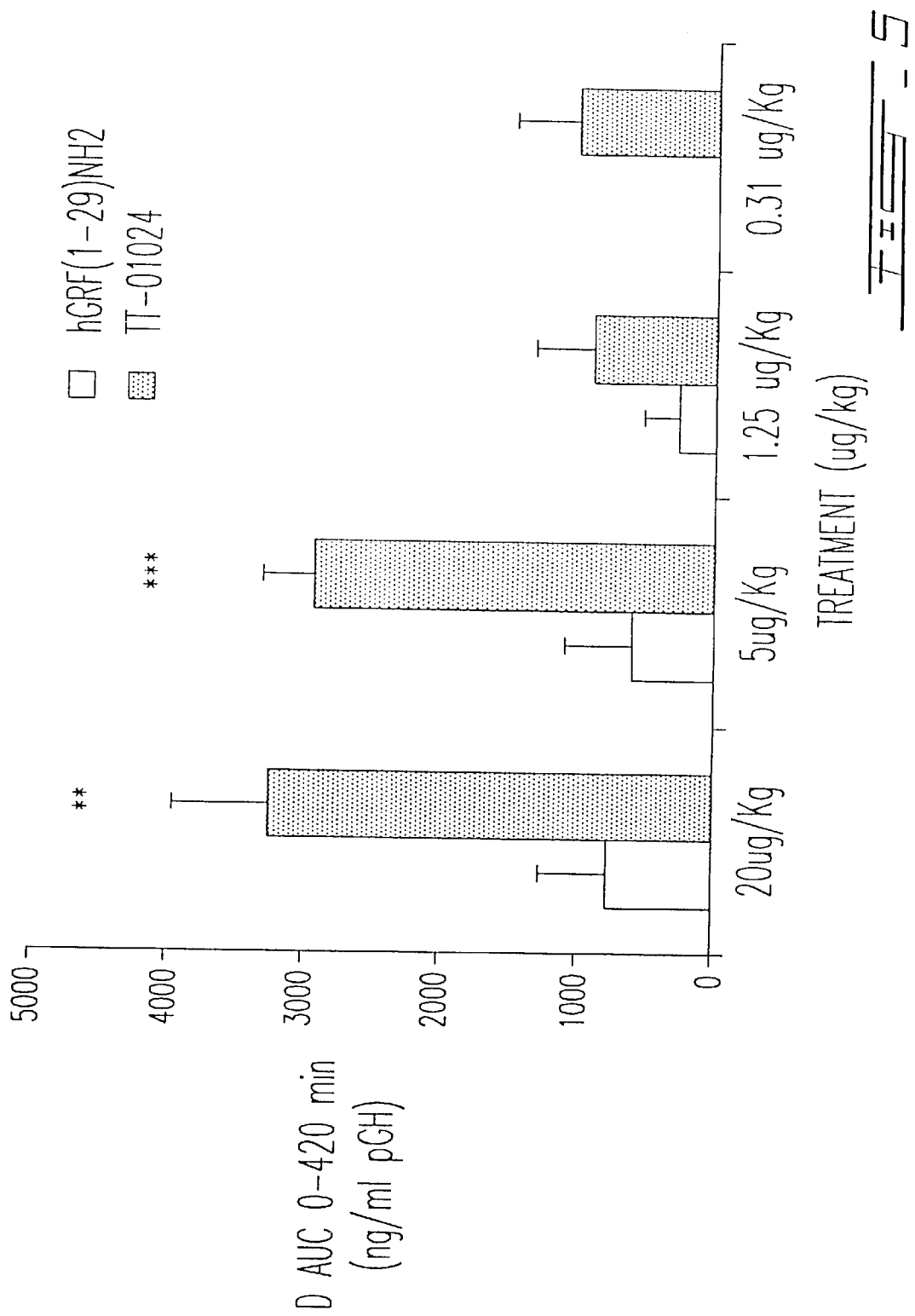
FIG. 5 is a graph showing the effect of various doses of hGRF(1–29)NH$_2$ vs [Hexenoyl trans-3]° hGRF(1–29)NH$_2$ (TT-01024) on the GH area under the curve over 420 minutes following S.C. administration (P<0.01 and *P<0.001 when compared to the basal period–60 to 0 min)

Results are shown in FIGS. 4 and 5. As shown in FIG. 4, the subcutaneous injection of 5 µg/kg hGRF(1–29)NH$_2$ induced a GH response in the first 60 minutes following administration, whereas the same injection of hexenoyl trans3-hGRF(1–29)NH$_2$ induced a GH response that was sustained for 240 minutes. The FIG. 5 illustrates the effect of various doses of the GRFs tested on the GH area under the curve over the study period, i.e. from 0 to 420 minutes following injection. Over this period, hGRF(1–29)NH$_2$ did not induce any significant GH response at any of the tested doses, whereas hexenoyl trans3-hGRF(1–29)NH$_2$ elicited significant increases of the GH AUC at 5 and 20 µg/kg. Altogether, these results suggest that hexenoyl trans3-hGRF (1–29)NH$_2$ is a highly potent GH secretagogue, even when subcutaneously administered.

EXAMPLE V

In accordance with a preferred embodiment of the present invention there is provided a hydrophobic GRF analog of formula A:

X—GRF-peptide                                                 A wherein;

the GRF peptide is a peptide of formula B

A1–A2-Asp-Ala-Ile-Phe-Thr-A8-Ser-Tyr-Arg-Lys-A13-Leu-A15-

Gln-Leu-A18-Ala-Arg-Lys-Leu-Leu-A24–A25-Ile-A27-A28-Arg-A30-R$_0$ (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;
A30 is a bond or any amino acid sequence of 1 to 15 residues;
R$_0$ is NH$_2$ or NH—(CH$_2$)n-CONH$_2$, with n=1 to 12 and;
X is cis or trans CH$_3$—CH$_2$—CH=CH—CH$_2$—CO—, or one element selected from a cis or a trans enantiomer or a racemic mixture of:

(1)
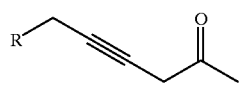

(2)

(3)

(4)

(5)
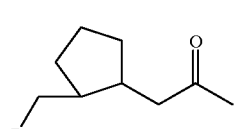

(6)
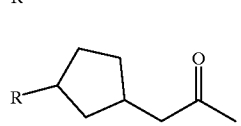

(7)
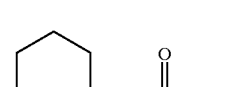

(8)

(9)
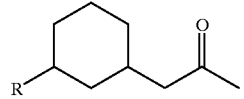

-continued

(10)
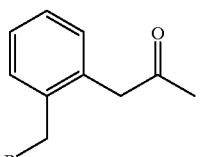

(11)
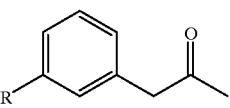

(12)
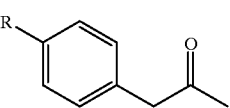

(13)
CH$_3$CH$_2$—C≡C—CH$_2$—CO

(14)
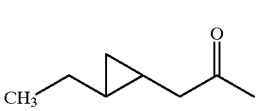

(15)
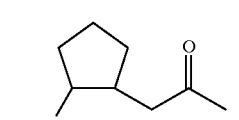

(16)
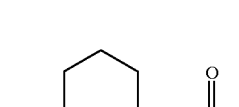

and

(17)

wherein R is a hydrogen or a lower alkyl.

Figure 6B:
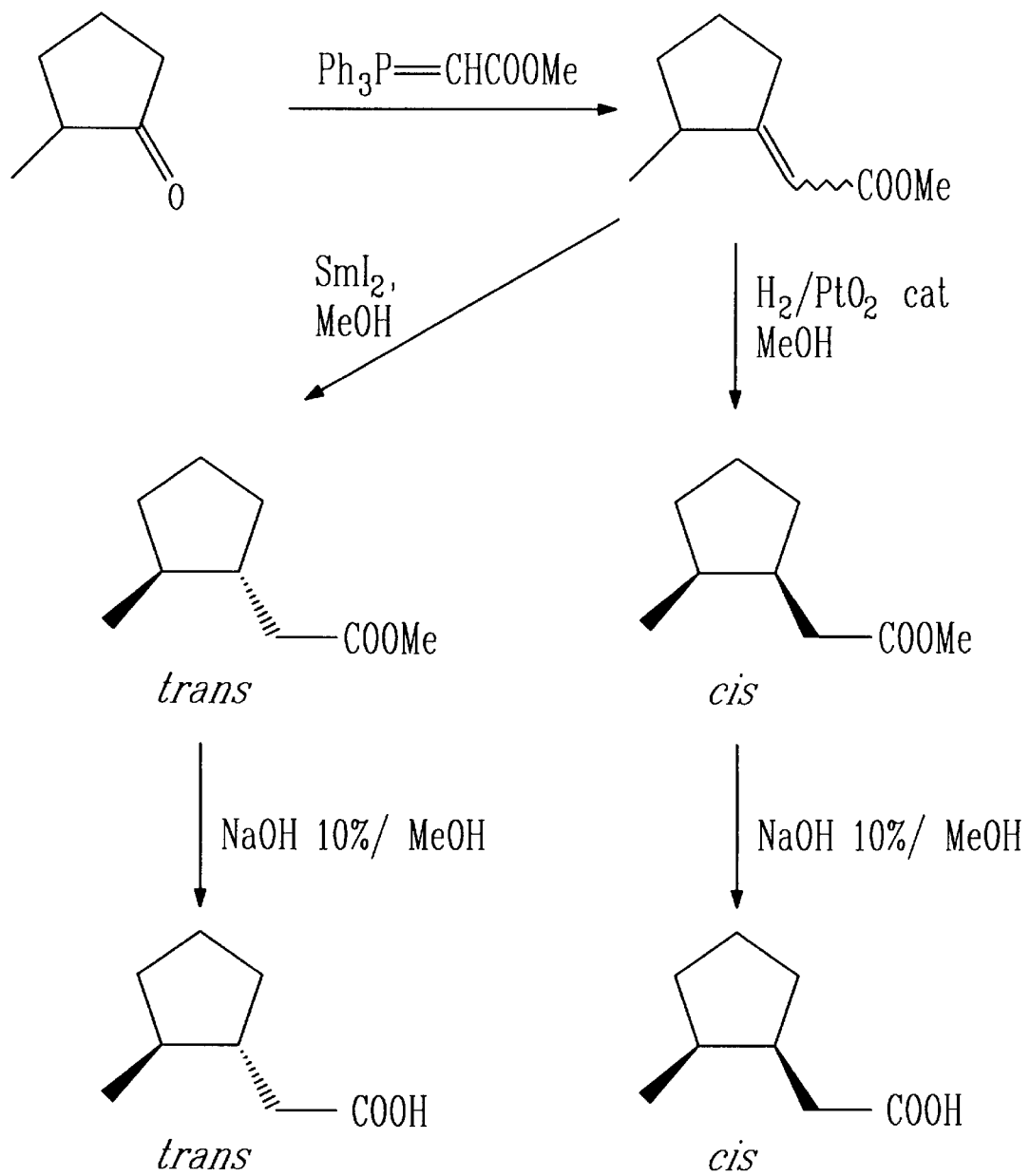

FIG. 6A to 6C illustrate examples of specific synthesis of GRF analogs with preferred radicals R in accordance with the present invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A hydrophobic GRF analog of formula A:

X—GRF-peptide                                 (A)

wherein;
the GRF peptide is a peptide of formula B:

A1-A2-Asp-Ala-Ile-Phe-Thr-A8-Ser-Tyr-Arg-Lys-A13-Leu-A15-Gln-Leu-A18-Ala-Arg-Lys-Leu-Leu-A24-A25-Ile-A27-A28-Arg-A30-R$_0$    (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;

A30 is a bond or any amino acid sequence of 1 up to 15 residues;
R$_0$ is NH$_2$ or NH—(CH$_2$)n—CONH$_2$, with n=1 to 12 and;
X is hydrophobic tail anchored via an amide bond at the N-terminus of said peptide, and said hydrophobic tail defining a backbone of 5 to 7 atoms;
wherein said backbone can be substituted by C$_{1-6}$ alkyl, C$_{1-6}$ cycloalkyl, or C$_{6-12}$ aryl;
and comprises at least one rigidifying moiety connected to at least two atoms of the backbone;
said rigidifying moiety selected from the group consisting of double bond, triple bond, saturated or unsaturated C$_{3-9}$ cycloalkyl, and C$_{6-12}$ aryl.

2. A pharmaceutical formulation for inducing growth hormone release which comprises as an active ingredient a GRF analog as claimed in claim 1, in association with a pharmaceutically acceptable carrier, excipient or diluent.

3. A method of increasing the level of growth hormone in a patient which comprises administering to said patient an effective amount of a GRF analog as claimed in claim 1.

4. A method for the diagnosis of growth hormone deficiencies in patients, which comprises administering to said patient a GRF analog as claimed in claim 1 and measuring the growth hormone response.

5. A method for the treatment of pituitary dwarfism or growth retardation in a patient, which comprises administering to said patient an effective amount of a GRF analog as claimed in claim 1.

6. A method for the treatment of wound or bone healing in a patient, which comprises administering to said patient an effective amount of a GRF analog as claimed in claim 1.

7. A method for the treatment of osteoporosis in a patient, which comprises administering to said patient an effective amount of a GRF analog as claimed in claim 1.

8. A method for improving protein anabolism in human or animal, which comprises administering to said human or animal an effective amount of a GRF analog as claimed in claim 1.

9. A method for inducing a lipolytic effect in human or animal inflicted with clinical obesity, which comprises administering to said human or animal an effective amount of a GRF analog as claimed in claim 1.

10. A method for the overall upgrading of somatroph function in human or animal, which comprises administering to said human or animal an effective amount of a GRF analog as claimed in claim 1.

* * * * *

UNITED STATES PATENT AND TRADEMARK OFFICE
Certificate

Patent No. 6,020,.311                                                                     Patented: February 1, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul Brazeau, Montreal, Canada; Denis Gravel, St-Lambert, Canada; Abdelkrim Habi, Quebec, Canada.

Signed and Sealed this Twenty-seventh Day of November 2007.

BRENDA BRUMBACK
*Supervisory Patent Examiner*
Art Unit 1654

UNITED STATES PATENT AND TRADEMARK OFFICE
Certificate

Patent No. 6,020,311                                                                                                                   Patented: February 1, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul Brazeau, Montréal, Canada; Denis Gravel, St-Lambert, Canada; and Abdelkrim Habi, Quebec, Canada.

Signed and Sealed this Twenty-ninth Day of January 2008.

CECILIA J. TSANG
                                                                                                                   *Supervisory Patent Examiner*
                                                                                                                           Art Unit 1654

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 44 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:1:

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40
```

(2) INFORMATION FOR SEQ ID NO:2:

(i) SEQUENCE CHARACTERISTICS:
      (A) LENGTH: 29 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:2:

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```